United States Patent
Barnes

(10) Patent No.: US 7,914,474 B2
(45) Date of Patent: Mar. 29, 2011

(54) DIP JOINT EXTENSION SPLINT

(75) Inventor: Darryl E. Barnes, Rochester, MN (US)

(73) Assignee: Darryl E. Barnes, M.D., Byron, MN (US)

( * ) Notice: Subject to any disclaimer, the term of this patent is extended or adjusted under 35 U.S.C. 154(b) by 231 days.

(21) Appl. No.: 12/244,084

(22) Filed: Oct. 2, 2008

(65) Prior Publication Data

US 2009/0099493 A1    Apr. 16, 2009

Related U.S. Application Data

(60) Provisional application No. 60/997,318, filed on Oct. 2, 2007.

(51) Int. Cl.
*A61F 5/00* (2006.01)
(52) U.S. Cl. .......................... 602/20; 602/22
(58) Field of Classification Search .............. 602/20–22; 128/879–880; 2/16, 161.8, 163
See application file for complete search history.

(56) References Cited

U.S. PATENT DOCUMENTS

| | | | | |
|---|---|---|---|---|
| 1,917,794 | A | * | 7/1933 | Brown ............... 602/22 |
| 2,548,378 | A | * | 4/1951 | Kleinfeld ........... 602/22 |
| 2,573,715 | A | * | 11/1951 | Kelly ............... 602/22 |
| 2,646,794 | A | * | 7/1953 | Baer ............... 602/22 |
| 4,932,396 | A | | 6/1990 | Garris |
| 5,077,870 | A | | 1/1992 | Melbye et al. |
| 5,417,692 | A | | 5/1995 | Goble et al. |
| 5,752,926 | A | | 5/1998 | Larson et al. |
| 5,807,291 | A | | 9/1998 | Larson et al. |
| 5,925,008 | A | | 7/1999 | Douglas |
| 6,076,238 | A | | 6/2000 | Arsenault et al. |
| 6,110,136 | A | | 8/2000 | Belkin |
| 6,692,435 | B1 | | 2/2004 | Choate |
| 6,692,452 | B2 | | 2/2004 | Chow |
| 6,716,186 | B1 | | 4/2004 | Singh et al. |
| 6,808,502 | B2 | | 10/2004 | Nguyen |
| D515,216 | S | | 2/2006 | Weber et al. |
| 7,041,106 | B1 | | 5/2006 | Carver et al. |

OTHER PUBLICATIONS

"A Patient's Guide to Mallet Finger Injuries," Montana Spine and Pain Center, eOrthopod, Medical Multimedia Group, L.L.C., Retrieved from the Internet Aug. 9, 2007:<URL:http://www.eorthopod.com/eorthopodV2/index/php/fuseaction/topics...>; 4 pgs.
"Buddy Taping," How to Describe an Injury, Retrieved from the Internet Aug. 9, 2007:<URL:http://www.siumed.edu/surgery/ortho/residents/injury.htm ...>; 1 pg.
"Conditions. Mallet Finger. Mallet (Baseball) Finger," 3 Point Products, © 2005, Retrieved from the Internet Aug. 9, 2007:<URL:http://www.3pointproducts.com/index.asp?pageid=3&conditionid=21...>; 2 pgs.
"Mallet Finger ("Baseball Finger" or "Extensor Tendon Injury")," (c)2000 DynoMed.com, Retrieved from the Internet Aug. 9, 2007:<URL:http://www.dynomed.com/encyclopedia/encyclopedia/hand_and_wri...>; 2 pgs. "Products. Oval-8® Finger Splint," 3 Point Products, © 2005, Retrieved from the Internet Aug. 9, 2007:<URL:http://www.3pointproducts.com/index.asp-?productid=43&pageid=2...>; 2 pgs.
"Products. Hand & Finger," Medex Medical Supplies Ltd., Retrieved from the Internet Aug. 9, 2007:<URL:http://www.medex.com.hk/gb/enpart/hand.htm...>; 2 pgs.
Rehak D.C., "Finger Injuries in Basketball Players," Hughston Health Alert,, Retrieved from the Internet Aug. 9, 2007: <URL:http://www.hughston.com/hha/a_16_4_2.htm...>; 2 pgs.

\* cited by examiner

*Primary Examiner* — Michael A. Brown
(74) *Attorney, Agent, or Firm* — Patterson Thuente Christensen Pedersen, P.A.

(57) ABSTRACT

Finger splints for use in connection with distal interphalangeal (DIP) joint fractures are disclosed. The splints include a ring element for positioning around a finger at a location proximal to the distal interphalangeal (DIP) joint and include an extension member that extends over the DIP joint and attaches to the fingernail.

20 Claims, 5 Drawing Sheets

DIP JOINT EXTENSION SPLINT

RELATED APPLICATION

The present application claims the benefit under 35 U.S.C. §119(e) of U.S. Provisional Patent Application Ser. No. 60/997,318 filed on Oct. 2, 2007 and titled DIP RING EXTENSION SPLINT, which is hereby incorporated by reference in its entirety.

BACKGROUND

The present invention relates generally to a finger splint. More particularly, the present invention relates to a distal interphalangeal joint extension splint.

The present invention may be for use in treating finger injuries, e.g., "Mallet Finger." "Mallet Finger" may occur when a force is directed at the distal finger resulting in an avulsion of the extensor tendon from the dorsum of the base of the distal phalanx. Currently, there are several splints on the market that are used to treat this injury.

Patient compliance is, however, an issue that may affect the outcome after treating these types of injuries, e.g., "Mallet Finger." In many cases, the splint should be left in place for 6-8 weeks without removal. Many patients, however, remove these splints before the injury has completely healed for several reasons, e.g., not knowing that the splint should stay in place for 6-8 weeks, to wash their finger, etc. Early removal of the splint may result in failed healing and/or deformity.

SUMMARY OF THE INVENTION

The splint according to the present invention may include a ring element positioned around a finger at a location proximal to the distal interphalangeal (DIP) joint and include an extension member that attaches to the fingernail. The extension member extends over the DIP joint between the ring element and the fingernail.

The extension member is preferably positioned only over the top surface of the finger. Doing so may result in increased compliance because the patient retains use of the finger tip sensation and is preferably able to wash the finger without removing the splint. Further, in various embodiments, tape may not need to be used to hold the splint on the finger, which may reduce the possibility of allergic reaction to the adhesive where it contacts the patient's skin.

In one aspect, the present invention provides a finger splint for use in the treatment of finger injuries, the splint including a ring element sized to fit around a finger at a location proximal to the distal interphalangeal (DIP) joint; an extension member having a proximal end attached to the ring element and a distal end located distally from the ring element; and an attachment element attached to the extension member proximate the distal end of the extension member, wherein the attachment element is capable of attaching the extension member to a fingernail when the ring element is positioned around a finger.

In various embodiments, the splint may include one or more of the following features: the extension member may define an extension member axis between the proximal end and the distal end of the extension member, and the distance between the attachment element and the ring element along the extension member axis is adjustable; the extension member may include an aperture proximate the distal end of the extension member, and the position of the attachment element is adjustable within the aperture; the aperture of the extension member may include grooves on an interior surface of the aperture, and the attachment element may include a releasable locking mechanism, wherein the releasable locking mechanism cooperates with the grooves of the aperture of the extension member to lock the attachment element in a selected position within the aperture; the finger splint may position the finger or a finger in hyperextension; the attachment element may include adhesive for attachment to a fingernail on which the splint is mounted; the extension member may be adjustably attached to the ring element such that the distance between the distal end of the extension member and the ring element can be adjusted proximate the ring element; the ring element may be a closed member; the ring element may be in the form of a slot; the distal end of the extension member may have a concave surface shaped to receive a fingertip; the ring element may be in the form of a male portion and a female portion, wherein the male portion and the female portion screw together; the ring element may include a tab and ratchet mechanism.

In another aspect, the present invention may provide a method of restraining a finger, the method including locating a splint on a finger, wherein the splint includes a ring element positioned proximally from the distal interphalangeal joint and an attachment element positioned adjacent a fingernail of the finger, with an extension member connecting the attachment element to the ring element; and attaching the attachment element of the splint to the fingernail while the ring element is positioned on the finger.

In another aspect, the present invention provides a finger splint for use in the treatment of finger injuries, the splint including a ring element sized to fit over a middle phalanx of a finger, wherein the ring element defines a finger axis; an extension member extending along and aligned with the finger axis between a proximal end and a distal end, wherein the extension member is attached to the ring element at the proximal end of the extension member; and an attachment element attached to the extension member proximate the distal end of the extension member, wherein the attachment element is located between the extension member and a fingernail of the finger. The attachment element is optionally adjustably attached to the extension member such that the distance between the ring element and the attachment element is adjustable.

In another aspect, the present invention provides a finger splint for use in the treatment of finger injuries, the splint including a ring element; an extension member extending from the ring element between a proximal end and a distal end, wherein the extension member is attached to the ring element proximate the proximal end of the extension member; and an attachment element attached to the extension member at the distal end of the extension member, and wherein the distal end of the attachment element includes adhesive. The attachment element is optionally adjustably attached to the extension member such that the distance between the ring element and the attachment element is adjustable.

In another aspect, the present invention provides a finger splint for use in the treatment of finger injuries, the splint including a ring element sized to fit over a middle phalanx of a finger, wherein the ring element defines a finger axis; an extension member extending along and aligned with the finger axis between a proximal end and a distal end, wherein the extension member is attached to the ring element at the proximal end of the extension member; and an attachment element attached to the extension member proximate the distal end of the extension member, wherein the attachment element is located between the extension member and a fingernail of the finger when the splint is located on a finger, and wherein the attachment element includes a mechanical fastener system. The attachment element is optionally adjustably attached to the extension member such that the distance between the ring element and the attachment element is adjustable.

The finger splints of the present invention may include an extension member that defines an extension member axis, wherein a position of the attachment element is adjustable along the extension member axis. The extension member may include an aperture proximate the distal end of the extension member, and the position of the attachment element is adjustable within the aperture. The aperture of the extension member may include grooves on an interior surface of the aperture, and the attachment element may include a releasable locking mechanism, wherein the releasable locking mechanism cooperates with the grooves of the aperture of the extension member to lock the attachment element in a selected position within the aperture.

The finger splints of the present invention may include one or more of the following features: the finger splint may position the finger or a finger in hyperextension; the finger splint may position the finger or a finger in about 3 degrees of hyperextension; the adhesive (if provided) may be pressure sensitive adhesive; the extension member may be adjustably attached to the ring element such that the distance between the distal end of the extension member and the ring element can be adjusted proximate the ring element; the extension member and the ring element may be a one piece, completely integral molded polymer article; the ring element may be a closed member; the ring element may include a slot; the length of the ring element may be adjustable; the distal end of the extension member may include a concave surface shaped to receive a fingertip; the ring element may include a male portion and a female portion, wherein the male portion and the female portion screw together; etc.

In another aspect, the present invention may provide a method of restraining a finger by locating a splint according to the invention on a finger, wherein the ring element of the splint is positioned proximally from the distal interphalangeal joint and the attachment element is positioned adjacent a fingernail of the finger; and attaching the attachment element of the splint to the fingernail. The attachment element include adhesive and/or a mechanical fastener system.

These and other features and embodiments of the invention may be described below in connection with some exemplary embodiments of the invention.

BRIEF DESCRIPTIONS OF THE DRAWING

DETAILED DESCRIPTION OF EXEMPLARY EMBODIMENTS

Figure 1:
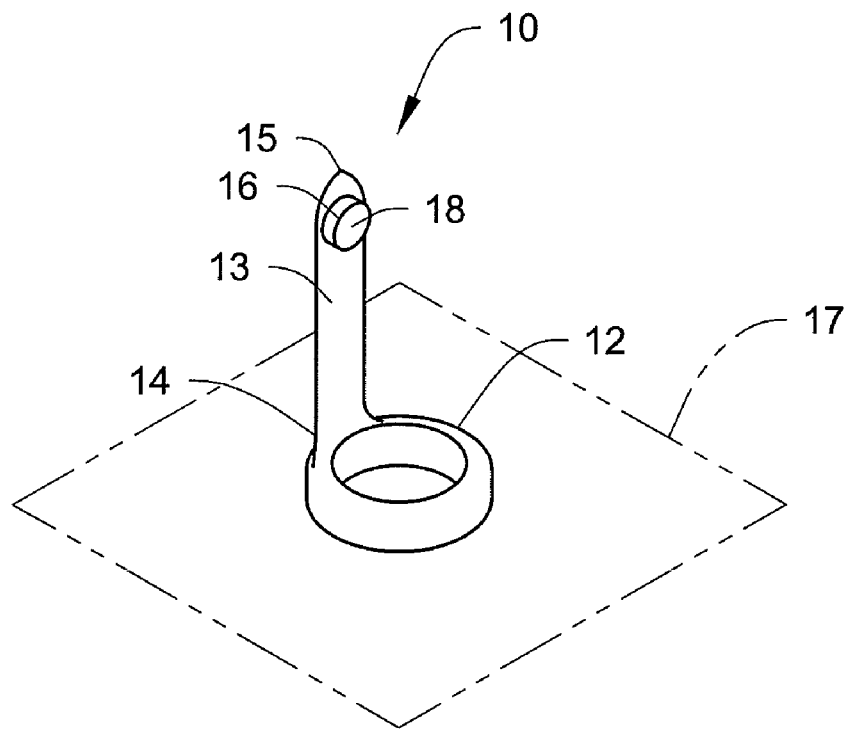
FIG. 1 depicts a perspective and illustrative view of one exemplary finger splint according to the current invention.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. The term "and/or" (if used) means one or all of the identified elements/features or a combination of any two or more of the identified elements/features.

The term "and/or" means one or all of the listed elements/features or a combination of any two or more of the listed elements/features.

FIG. 1 depicts a perspective and illustrative view of one exemplary finger splint according to the current invention. The finger splint 10 may include a ring element 12, an extension member 13, and an attachment element 16.

The ring element 12 may be a solid, continuous cylinder as depicted, which is generally sized to fit over the middle phalanx of a finger. At least in one embodiment, the ring element 12 may be adjustable in length (along an axis defined by the finger), diameter, and/or circumference to accommodate different sizes and/or shapes of fingers. Further, at least in one embodiment, the ring element 12 may not be continuous, e.g., the ring element may include a slot or a notch such that the ring element extends less than 360 degrees around the finger. Still further, at least in one embodiment, the ring element 12 may not be circular, e.g., the ring element 12 may be elliptically or otherwise shaped to conform to the shape of a finger. Still further, in at least one embodiment, the ring element 12 may not be solid, e.g., the ring element 12 may be substantially hollow.

The extension member 13 in the depicted embodiment is a substantially straight member extending from a proximal end 14 to a distal end 15. The proximal end 14 of the extension member 13 is attached to the ring element 12 and the extension member 13 extends to the distal end 15 substantially perpendicular to a plane 17 defined by the ring element 12 (which plane is also substantially perpendicular to a finger axis of a finger on which the ring element is positioned). In this embodiment, the extension member 13 is integral with the ring element 12, i.e., the extension member 13 and the ring element 12 are provided as a one-piece, completely integral article that may be molded or otherwise formed (e.g., machined, sintered, etc.) from any suitable material (e.g., metal, polymer, ceramic, composites, etc.).

The ring element 12 and the extension member 13 may not be integral and may, instead, be separate pieces that may be fixedly and/or adjustably attached to each other. Although not shown, separate extension members and ring elements may be attached to each other through an adjustment mechanism so that the distance between the distal end 15 of the extension member 13 and the ring element 12 may be adjusted where, e.g., the extension member 13 attaches to the ring element 12.

Figure 2:
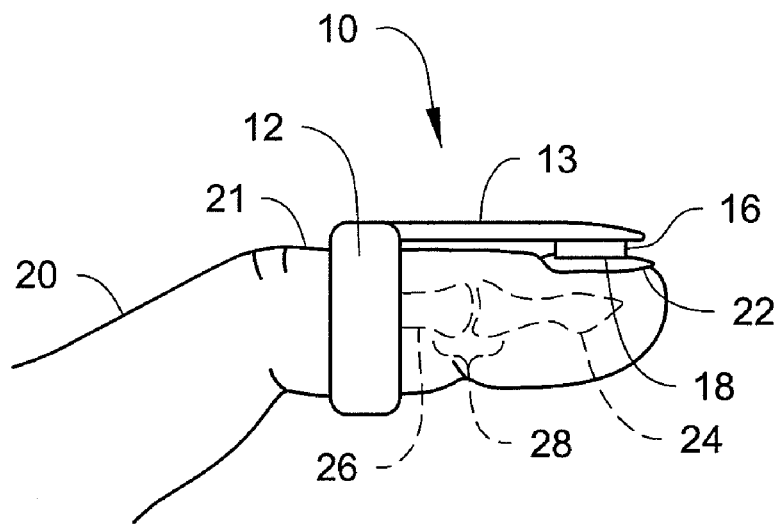
FIG. 2 is a side view of the splint of FIG. 1 in place on a finger.

In some embodiments the extension member 13 may not extend from the ring element 12 in a substantially perpendicular direction relative to plane 17, e.g., the extension member may extend from the plane at an angle that is not perpendicular to the plane 17. In other variations, the extension member 13 may include, e.g., multiple bends or may be continuously curved instead of being substantially straight as depicted in FIGS. 1 & 2.

In still other variations, the extension members of finger splints according to the present invention may be malleable such that the orientation of the extension member with respect to the ring element can be adjusted. The malleability may be provided by, e.g., constructing the extension member and/or ring element out of materials such as metals, plastics (potentially thermoplastics that can be heated to increase malleability), etc. Such malleability may also be useful for adjusting the shape of the extension member such that it avoids contact with the finger between the ring element and the fingernail.

The attachment element 16 as depicted in FIG. 1 is located near the distal end 15 of the extension member 13 on the side of the extension member facing the interior of the ring element 12. Generally, the attachment element 16 is used to fixedly attach the splint 10 to the fingernail of a finger on which the splint is mounted. The surface 18 of the attachment element 16 may preferably be adhered to the fingernail. In at least one embodiment, the attachment element 16 may include any suitable adhesive material, e.g., cyanoacrylate, epoxy, acrylic adhesives, etc. It may be preferred that the adhesive be a pressure sensitive adhesive.

In the depicted embodiment, the attachment element 16 is attached to the extension member 13 at a fixed, stationary location. The attachment element 16 may, however, be adjustably attached to the extension member 13, i.e., the position of the attachment element 16 relative to the ring element 12 may be adjustable. For example, the extension member 13 and the attachment element 16 may be attached to each other using an adjustment mechanism so that the distance between the attachment element 16 and the ring element 12 may be adjusted. In another alternative, an adjustment mechanism may be located at the juncture between the ring element 12 and the extension member 13 (with the attachment element 16 in a fixed position on the extension member 13). In still another alternative, the adjustment mechanism may be in a form where the length of the extension member 13 is adjustable, e.g., the extension member 13 may have a telescoping structure, etc.

Although depicted as a separate body in FIGS. 1 & 2, the attachment element 16 may be integral with the extension member 13. In perhaps its simplest form, the attachment element 16 may be provided as a mass of adhesive that may or may not have a visually discernable thickness (for example, the attachment element may be in the form a thin layer of cyanoacrylate adhesive located between the extension member 13 and the fingernail 22). In other embodiments, the attachment element 16 may have a thickness and a volume as depicted in FIGS. 1 & 2. In such embodiments, the attachment element 16 may be rigid or resilient. For example, the attachment element 16 may include a resilient body that carries the adhesive used to attach the splint to a fingernail or the body of the attachment element 16 may consist essentially of adhesive. If provided as a resilient body, the resilience of the attachment element 16 may provide some compliance between the extension member 13 and the fingernail 22 to which the device is attached.

In still other embodiments, the attachment element may include a mechanical fastener system that includes two components that attach to each other. Examples of some potentially suitable mechanical fastener systems may include hook and loop closures (examples of which are available under the tradename VELCRO), mating fastener elements, etc. (see, e.g., U.S. Pat. Nos. 5,077,870; 6,076,238; etc.). If a mechanical fastener system is used, it may be preferred that one component be attached (e.g., adhesively) to the fingernail and the mating component be attached to the extension member. Attachment of the two components to each other then serves to attach the fingernail to the extension member.

FIG. 2 depicts a perspective and illustrative view of exemplary splint 10 in position on a finger 20. The bones of the finger 20 are depicted to better illustrate the functionality of the splint 10. More specifically, the finger 20 includes skin 21, a fingernail 22, a distal phalanx 24, a middle phalanx 26, and a distal interphalangeal joint 28. As shown in this depiction, the ring element 12 of the splint 10 is located around the middle phalanx 26 of the finger 20 at a location proximal to the distal interphalangeal joint 28. The extension member 13 extends from the ring element 12 to the tip of the distal phalanx 24.

The attachment element 16, as shown, is attached to the fingernail 22. The attachment element 16 may be used to retain the splint 10 on the finger 20. In turn, the splint 10 may prohibit substantial movement of the distal phalanx 24 at the distal interphalangeal joint 28 as to, e.g., allow an extensor tendon to heal. The adhesive of the attachment element 16 preferably remains selectively attached to the fingernail 22. For example, the adhesive may remain attached for a fixed time period based on average deterioration of the adhesive. Further, for example, the adhesive may remain attached until a releasing compound (e.g., a solvent) is used on the adhesive. Still further, for example, the adhesive may be selected such that it remains attached to the fingernail 22 under a selected amount of force. The selected force may, for example, be greater than the force that a finger may apply to the distal phalanx 24 of that finger.

In at least one embodiment, the splint 10 may secure the distal phalanx 24 in a position that supplies hyperextension, i.e., movement beyond the normal range of motion of the distal phalanx 24 in the dorsal direction. It may be preferred that the splint 10 be capable of securing the distal phalanx 24 in about 3 degrees or more of hyperextension. In another characterization, the splint 10 may secure the distal phalanx 24 in some amount of hyperextension up to about, e.g., 5, 10, or even 15 degrees of hyperextension.

Figure 3:
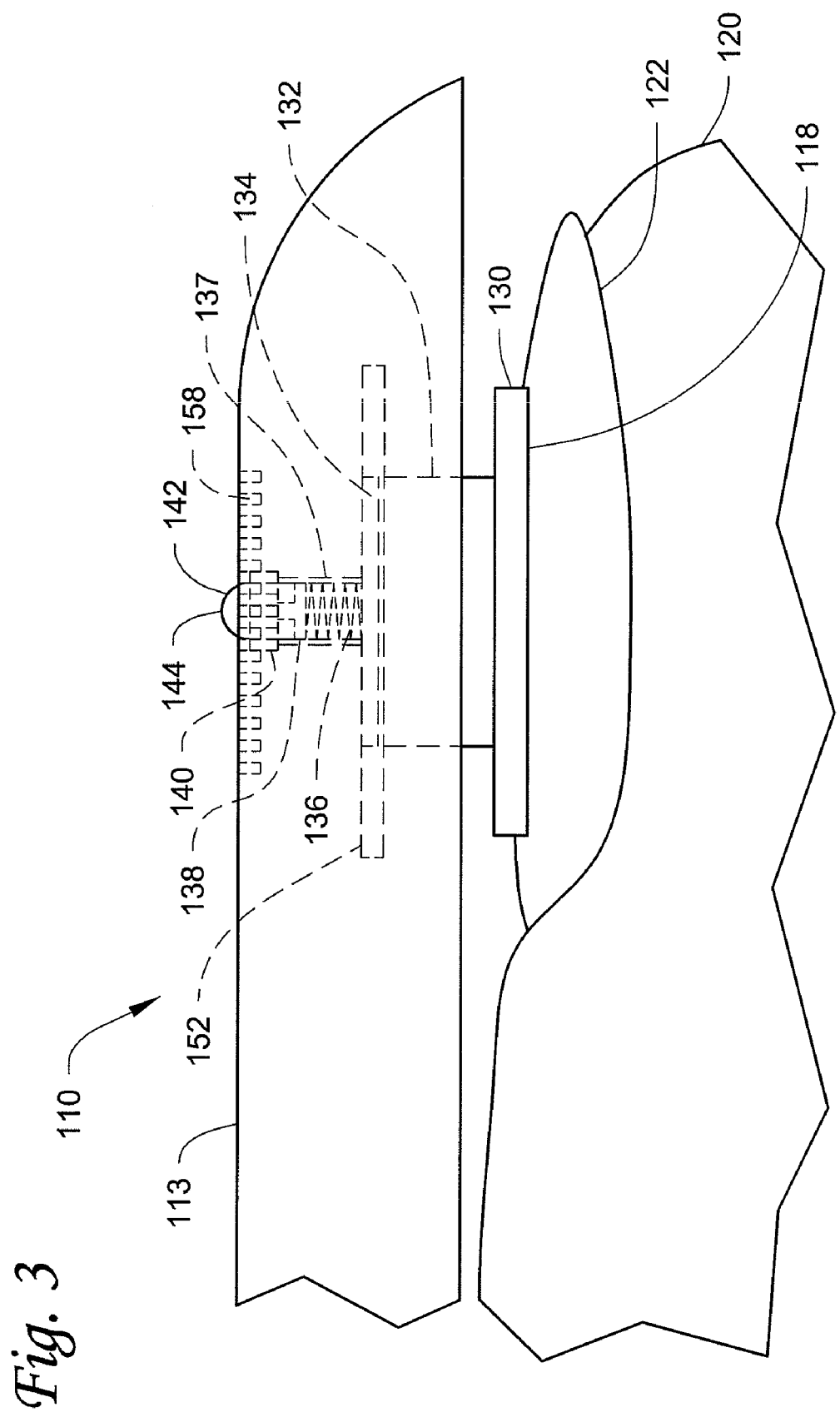
FIG. 3 is a partial side view another exemplary embodiment of a finger splint on a finger.
Figure 4:
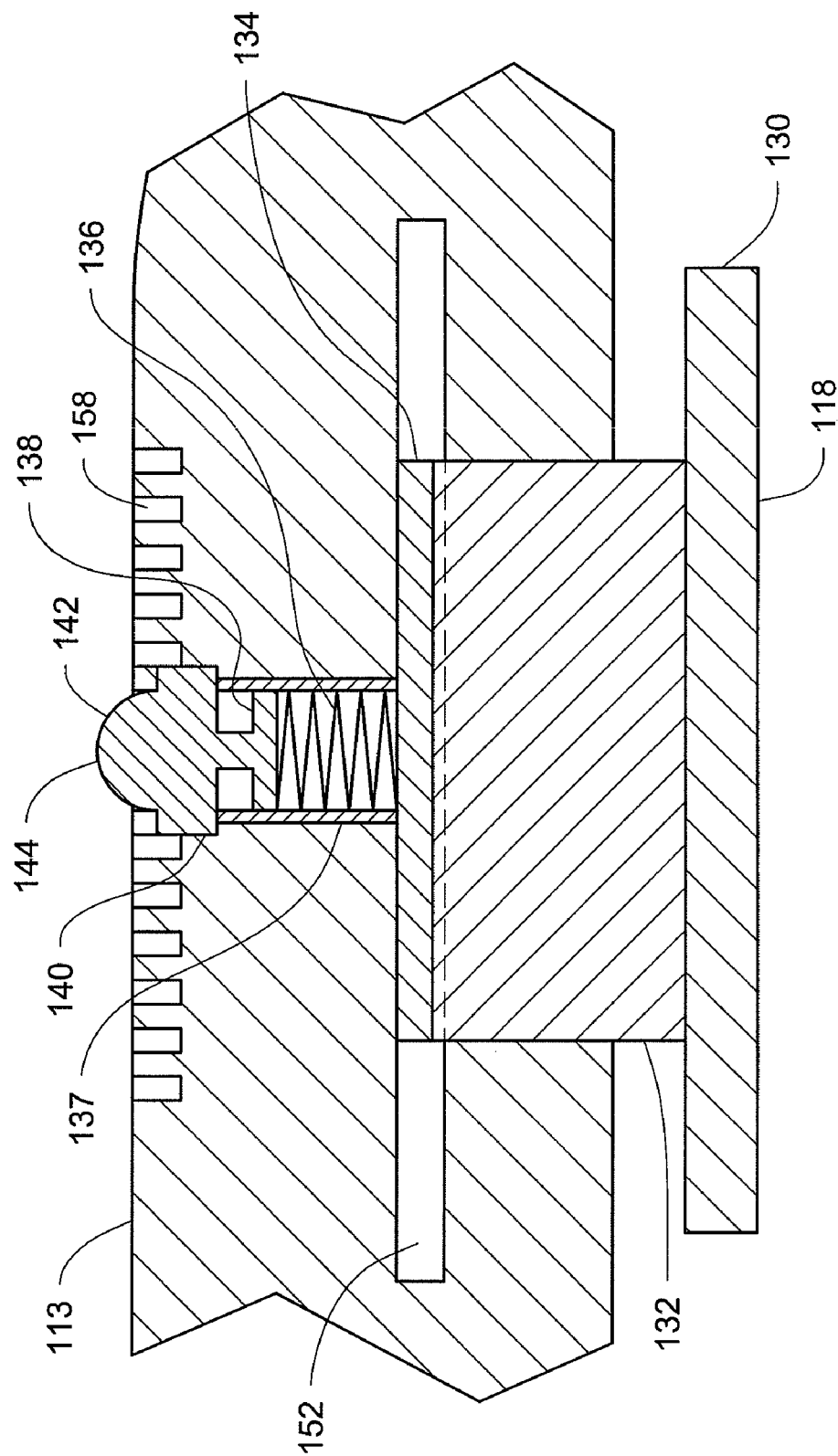
FIG. 4 is an enlarged cross-sectional view of a portion of the extension member depicted in FIG. 3.

FIG. 3 is a partial side view another exemplary embodiment of a finger splint 110 on a finger 120 according to the current invention. FIG. 4 is an enlarged view of the attachment element 116 and a portion of the extension member 113 of FIG. 3. Only the distal portion of the finger 120 and distal portion of the finger splint 110 are shown in FIGS. 3 & 4.

In the embodiment depicted in FIGS. 3 & 4, the attachment element 116 is movable along the length of the extension member 113. This feature may be useful because, as the fingernail 122 grows and the attachment element 116 remains attached to the fingernail 122, the splint 110 will move distally with the growth of the fingernail 122. In turn, this movement may reposition the splint 110, which may hamper the functionality of the splint 110, e.g., the ring element portion of the splint 110 may be moved from the middle phalanx to or past the distal interphalangeal joint, which may reduce the effectiveness of the splint 110 at immobilizing the distal interphalangeal joint.

One embodiment of a finger splint that may address the problem of fingernail growth is depicted in FIGS. 3 & 4. The attachment element 116 may be movable relative to the extension member 113. As the fingernail 122 grows and moves the splint 110 out of its proper position, the attachment element 116 may be unlocked, repositioned, and re-locked as to properly function, e.g., to substantially immobilize the distal interphalangeal joint. These adjustments are preferably performed without removing the splint 110.

In the depicted mechanism, an adhesive plate 130 is attached to the fingernail 122 of the finger 120. The adhesive plate 130 may be formed of a resilient or rigid material. The surface 118 of the adhesive plate 130 is the portion of the adhesive plate 130 that contacts the fingernail 122 and may be adhered to the fingernail 122. The surface 118 may be adhesive itself or an adhesive substance may be applied to the surface 118 before attachment to the fingernail 122.

The side of the adhesive plate 130 opposite the surface 118 is attached to a slide 132. The slide 132 is located within a slot formed in the extension member 113. The slot may preferably extend through the extension member from the anterior side (i.e., the finger side) to the posterior side. An upper portion of the slide 132 includes a rail 134 that protrudes from the sides of the slide 132. The rail 134 cooperates with structure 152 in the slot to retain the attachment element 116 within the slot. Generally, the slot is sized to precisely fit the slide element 132 within so as to allow limited (if any) lateral movement (i.e., movement that is not along the longitudinal axis defined by the extension member 113).

A tubular element 137 is attached to the top of the slide 132 and extends towards to the posterior side of the extension member 113. The tubular element 137 may have a circular cross section, square cross section, or any other cross-sectional shape.

The adhesive plate 130, the slide 132, the rail 134, and the tubular element 137 may be integral with each other (e.g., molded as a one-piece, completely integral unit). Alternatively, the adhesive plate 130, the slide 132, the rail 134, and the tubular element 137 may be provided in two or more separate parts that are attached to one another. The adhesive plate 130, the slide 132, the rail 134, and the tubular element 137 may be formed of the same material, or different materials. Generally, these elements may be formed of rigid materials.

A resilient member 136 may be provided within the tubular element 137. Although in this embodiment, the resilient member 136 is depicted as a coil spring, the resilient member 136 may be formed of any resilient material in any shape as would be known by one having skill in the art. For example, the resilient member may be formed of foam, silicone elastomer, rubber, etc.

The top of the resilient member 136 is adjacent to the plunger portion 138 of the button 142. The button 142 has a plunger portion 138, a grooved portion 140, and a top 144. The plunger portion 138, the grooved portion 140, and the top 144 may be of one-piece, completely integral construction or may be separate parts that are fixedly attached.

The grooved portion 140 of the button 142 may be sized to fit within the grooves 158 of the slot of the extension member 113 so as to immobilize the attachment element 116 with the extension member 113. When the resilient member 136 is in an uncompressed state, the grooved portion 140 of the button 142 preferably mates with the grooves 158 of the slot of the extension member 113 to prevent movement of the attachment element 116 relative to the extension member 113. Movement of the attachment element 116 may be accomplished by depressing the top 144 of the button 142 to compress the resilient member 136 and move the grooved portion 140 of the button 142 out of the grooves 158 of the slot. Depressing the top 144 of the button 142 in this manner will unlock the attachment element 116 from the extension member 113, which allows the location of the attachment element 116 along the extension member 113 to be adjusted to, e.g., compensate for fingernail growth.

Figure 5:
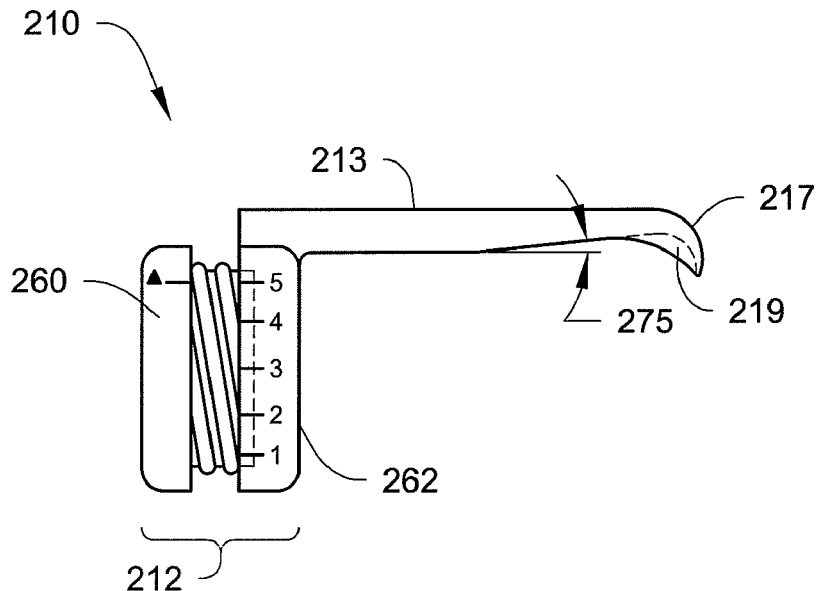
FIG. 5 is a side view of another exemplary splint according to the present invention.
Figure 6:
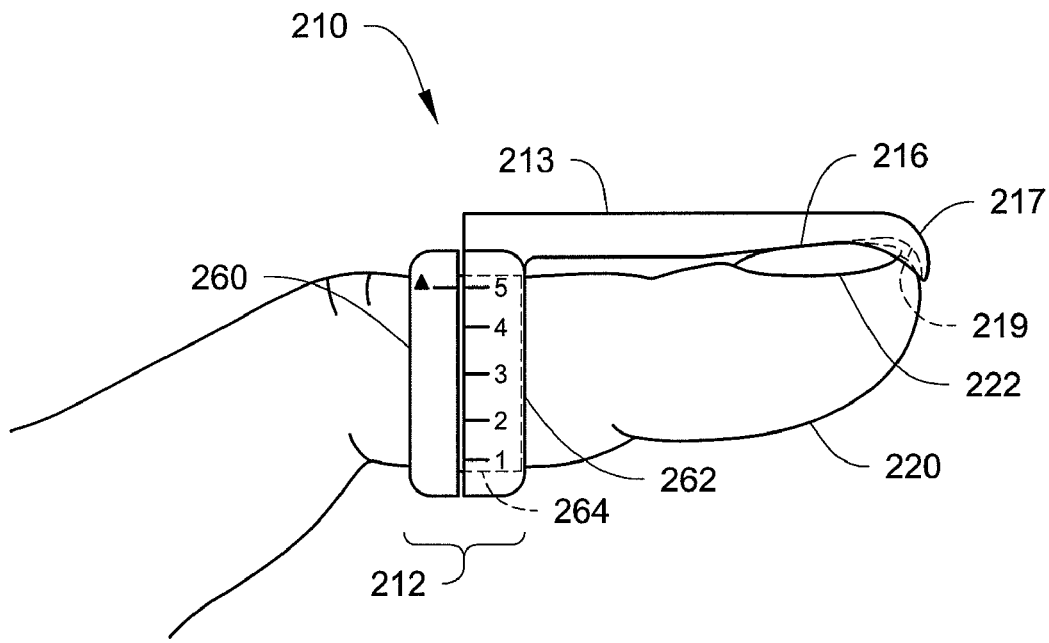
FIG. 6 is a side view of the splint of FIG. 5 in place on a finger.

Another exemplary embodiment of a finger splint 210 that may address the problem of fingernail growth is depicted in FIGS. 5 & 6. The ring element 212 is extendable along its longitudinal axis so that when the fingernail 222 of finger 220 grows and moves the splint 210, the distance between the attachment element 216 and the ring element 212 may be adjusted.

The extension member 213 extends from the ring element 212 to the tip of the finger 220 as to support the joint between the distal interphalangeal joint. This embodiment includes an optional concave portion 219 of the extension member 213 formed near the distal end 217 of the extension member 213 and sized to receive the tip of finger 220. The concave portion 219 may have many uses such as to partially secure the finger 220 within the splint 210 and/or to protect the finger 220 from "jamming." In this embodiment, the extension member 213 extends from the ring element 212 substantially perpendicular to a plane formed through the ring element 212.

Near the midsection of the extension member 213, i.e., between the concave portion 217 and the ring element 212, the extension member 213 tapers as to form an angle 275. The angle 275 may be, e.g., greater than zero degrees to about 25 degrees. The extension member 213 may preferably position the distal interphalangeal joint of the finger 220 in hyperextension as shown in FIG. 6.

In the adjustment mechanism associated with this embodiment, the ring element 212 has two sections: a threaded male section 260 and a threaded female section 262. The male section 260 mates the female section 262 and the inner male section 260 may preferably be positioned proximal to the distal interphalangeal joint to properly position the splint 210. In FIG. 5, the male section 260 is partially unscrewed from the female section 262 as to extend the ring element 212 and increase the distance between the inner male section 260 and the attachment element 216. In FIG. 6, the male section 260 is fully screwed into the female section 262. Dotted line 264 signifies where the screw portion of the male section 260 resides within the female section 262.

The ring element 212 may include indicia on the male section 260 and the female section 262 that correspond with each other as to show a user the distance the male section 260 has been screwed into the female section 262.

Figure 7:
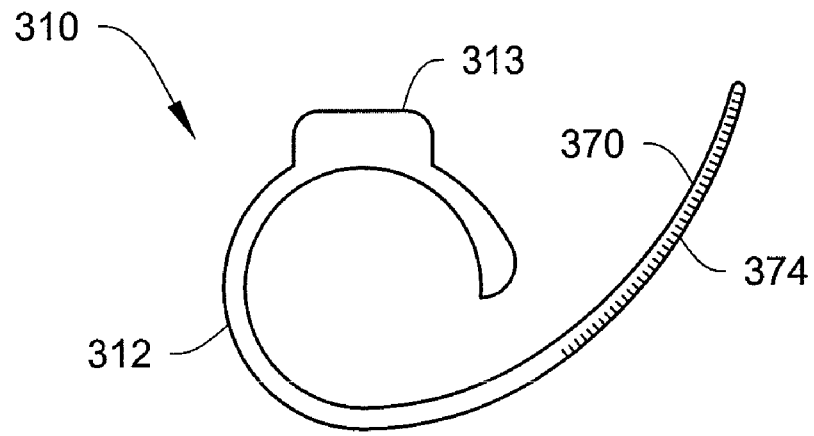
FIG. 7 is an end view of another exemplary embodiment of a splint according to the present invention.
Figure 8:
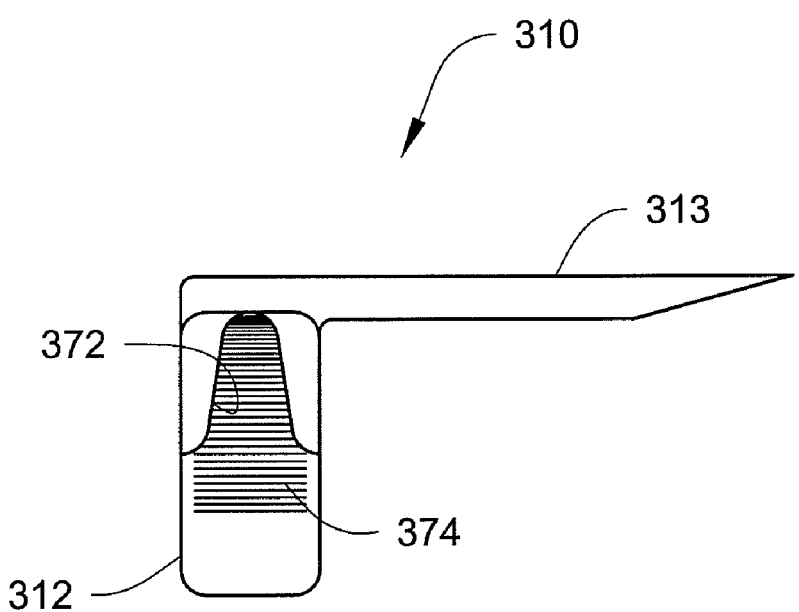
FIG. 8 is a side view of the splint of FIG. 7.

Another exemplary embodiment of a finger splint according to the present invention is depicted in FIGS. 7 and 8, with FIG. 7 being a view taken along the axis of the extension member 313 of the finger splint 310 and FIG. 8 being a side view of the finger splint 310. The finger splint 310 includes a ring element 312 that includes a tab 370 that fits within a slot 372 to form a closed loop so that the ring element 312 can be retained in place on a finger. The tab 370 may preferably include a ratchet mechanism that includes slotted surface 374 that cooperates with a pawl (not shown) located in the slot 372 to prevent removal of the tab 370 from the slot 372.

In essence, the tab 370 and slot 372 function in the manner of a cable tie. In some embodiments, the ratchet mechanism may include structure that allows for release of the pawl (if, e.g., the tab 370 is pulled too far through the slot 372). As seen in FIG. 8, the portion of the tab 370 may be removed after the ring element 312 is in a select position. Although the tab 370 is depicted as an integral component with the ring element 312, the ring element 312 may be provided separately from the tab 370 such that the tab 370 is provided in the form of a discrete article (e.g., a cable tie) that cooperates with the ring element 312 (e.g., is fitted in a slot, channel, through guides, etc.).

Although the exemplary embodiments described herein depict the finger splint utilized with a finger, the finger splint may be used on other appendages, such as, but not limited to, toes on a foot. Further, although the exemplary embodiments described herein depict the finger splint utilized with the distal interphalangeal joint, the finger splint may be used on other joints, such as, but not limited to, the proximal interphalangeal joint.

The complete disclosure of the patents, patent documents, and publications cited in the Background, the Summary, the Detailed Description of Exemplary Embodiments, and elsewhere herein are incorporated by reference in their entirety as if each were individually incorporated. Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. Thus, the invention is limited only by the following claims and equivalents thereto.

The invention claimed is:

1. A finger splint for use in the treatment of finger injuries, the splint comprising:
   a ring element sized to fit around a finger at a location proximal to the distal interphalangeal (DIP) joint;
   an extension member comprising a proximal end attached to the ring element and a distal end located distally from the ring element; and
   an attachment element attached to the extension member proximate the distal end of the extension member, wherein the attachment element is capable of attaching the extension member to a fingernail when the ring element is positioned around a finger;
   wherein the extension member defines an extension member axis between the proximal end and the distal end of the extension member, the extension member comprises an aperture proximate the distal end of the extension member, the distance between the attachment element and the ring element along the extension member axis is adjustable, and the position of the attachment element is adjustable within the aperture; and
   wherein the aperture of the extension member comprises grooves on an interior surface of the aperture, and the attachment element comprises a releasable locking mechanism, wherein the releasable locking mechanism cooperates with the grooves of the aperture of the extension member to lock the attachment element in a selected position within the aperture.

2. The finger splint according to claim 1, wherein the finger splint positions the finger or a finger in hyperextension.

3. The finger splint according to claim 1, wherein the attachment element comprises adhesive for attachment to a fingernail on which the splint is mounted.

4. A finger splint for use in the treatment of finger injuries, the splint comprising:
   a ring element sized to fit around a finger at a location proximal to the distal interphalangeal (DIP) joint;
   an extension member comprising a proximal end attached to the ring element and a distal end located distally from the ring element; and
   an attachment element attached to the extension member proximate the distal end of the extension member, wherein the attachment element is capable of attaching the extension member to a fingernail when the ring element is positioned around a finger;
   wherein the ring element comprises a male portion and a female portion, wherein the male portion and the female portion screw together.

5. The finger splint according to claim 1, wherein the ring element comprises a closed member.

6. The finger splint according to claim 1, wherein the ring element comprises a slot.

7. The finger splint according to claim 1, wherein the distal end of the extension member comprises a concave surface shaped to receive a fingertip.

8. The finger splint according to claim 4, wherein the extension member is adjustably attached to the ring element such that the distance between the distal end of the extension member and the ring element can be adjusted proximate the ring element.

9. A finger splint for use in the treatment of finger injuries, the splint comprising:
   a ring element sized to fit around a finger at a location proximal to the distal interphalangeal (DIP) joint;
   an extension member comprising a proximal end attached to the ring element and a distal end located distally from the ring element; and
   an attachment element attached to the extension member proximate the distal end of the extension member, wherein the attachment element is capable of attaching the extension member to a fingernail when the ring element is positioned around a finger;
   wherein the ring element comprises a tab and ratchet mechanism.

10. A method of restraining a finger, the method comprising:
    locating a splint according to claim 1 on a finger, wherein the ring element is positioned proximally from the distal interphalangeal joint and the attachment element is positioned adjacent a fingernail of the finger; and
    attaching the attachment element of the splint to the fingernail while the ring element is positioned on the finger.

11. A method according to claim 10, wherein the attaching comprises adhesively attaching the splint to the fingernail.

12. A finger splint for use in the treatment of finger injuries, the splint comprising:
    a ring element comprising a tab and ratchet mechanism;
    an extension member extending from the ring element between a proximal end and a distal end, wherein the extension member is attached to the ring element proximate the proximal end of the extension member; and
    an attachment element attached to the extension member at the distal end of the extension member, and wherein the distal end of the attachment element comprises adhesive;
    and wherein, optionally, the attachment element is adjustably attached to the extension member such that the distance between the ring element and the attachment element is adjustable.

13. The finger splint according to claim 12, wherein the extension member defines an extension member axis between the proximal end and the distal end of the extension member, and wherein the distance between the attachment element and the ring element along the extension member axis is adjustable.

14. The finger splint according to claim 12, wherein the finger splint positions the finger or a finger in hyperextension.

15. The finger splint according to claim 12, wherein the distal end of the extension member comprises a concave surface shaped to receive a fingertip.

16. The finger splint according to claim 12, wherein the adhesive comprises pressure sensitive adhesive.

17. The finger splint according to claim 4, wherein the attachment element comprises adhesive for attachment to a fingernail on which the splint is mounted.

18. The finger splint according to claim 4, wherein the male portion and the female portion adjustably screw and unscrew together such that a distance between the attachment element and the male portion is adjustable.

19. The finger splint according to claim 4, wherein the distal end of the extension member comprises a concave surface shaped to receive a fingertip.

20. The finger splint according to claim 18, wherein the ring element contains a screwing distance indicia the male portion and the female portion to signify an adjustment position between the male portion and the female portion.

* * * * *